(12) United States Patent
Watabe et al.

(10) Patent No.: US 9,031,794 B2
(45) Date of Patent: May 12, 2015

(54) AUTOMATIC ANALYZING SYSTEM

(75) Inventors: Osamu Watabe, Mito (JP); Masashi Akutsu, Hitachinaka (JP); Hitoshi Tokieda, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 102 days.

(21) Appl. No.: 13/575,169

(22) PCT Filed: Jan. 28, 2011

(86) PCT No.: PCT/JP2011/051739
§ 371 (c)(1),
(2), (4) Date: Jul. 25, 2012

(87) PCT Pub. No.: WO2011/093442
PCT Pub. Date: Aug. 4, 2011

(65) Prior Publication Data
US 2012/0294765 A1 Nov. 22, 2012

(30) Foreign Application Priority Data
Jan. 28, 2010 (JP) .................................. 2010-016142

(51) Int. Cl.
G01N 35/02 (2006.01)
G01N 35/00 (2006.01)
G01N 35/04 (2006.01)

(52) U.S. Cl.
CPC ........ *G01N 35/0092* (2013.01); *G01N 35/0095* (2013.01); *G01N 35/026* (2013.01); *G01N 35/04* (2013.01); *G01N 2035/00326* (2013.01); *G01N2035/0415* (2013.01); *G01N 2035/0462* (2013.01)

(58) Field of Classification Search
CPC .......... G01N 35/0092; G01N 35/0095; G01N 35/026; G01N 35/04; G01N 2035/00326; G01N 2035/0415; G01N 2035/0462

USPC ............ 700/266; 702/19, 22, 31, 32; 422/62, 422/65–67

See application file for complete search history.

(56) References Cited

U.S. PATENT DOCUMENTS

| 8,252,233 B2 * | 8/2012 | Tokieda et al. ................. 422/65 |
| 2004/0014227 A1 * | 1/2004 | Frederick et al. ............... 436/43 |
| 2009/0162247 A1 | 6/2009 | Tokieda et al. |
| 2009/0191095 A1 * | 7/2009 | Nakamura ...................... 422/67 |

FOREIGN PATENT DOCUMENTS

| JP | 09-033539 A | 2/1997 |
| JP | 2004-279357 A | 10/2004 |
| JP | 2006-038881 A | 2/2006 |
| JP | 2008-281453 A | 11/2008 |
| JP | 2009-150859 A | 7/2009 |

* cited by examiner

*Primary Examiner* — Shogo Sasaki
(74) *Attorney, Agent, or Firm* — Mattingly & Malur, PC

(57) ABSTRACT

There is provided an analysis apparatus in which congestion does not occur and whose analysis efficiency is high as a whole even when the apparatus is an automatic analyzing apparatus to which a plurality of functional modules having different functions and process performances from each other are connected. Also, there is provided an automatic analysis system in which, even when a new functional module is added, it is not required to consider influence on the existing functional modules and restructure a carrying plan or others for improving process performances as a whole. Buffer units paired with the respective functional modules are connected to a specimen carrying line, and an operating-section computer issues an instruction for carrying to the respective functional modules in accordance with requests for specimens, so that carrying-in/out operations are performed as managing respective carrying-possible states among the buffer units and functional modules.

22 Claims, 12 Drawing Sheets

AUTOMATIC ANALYZING SYSTEM

TECHNICAL FIELD

Figure 1:
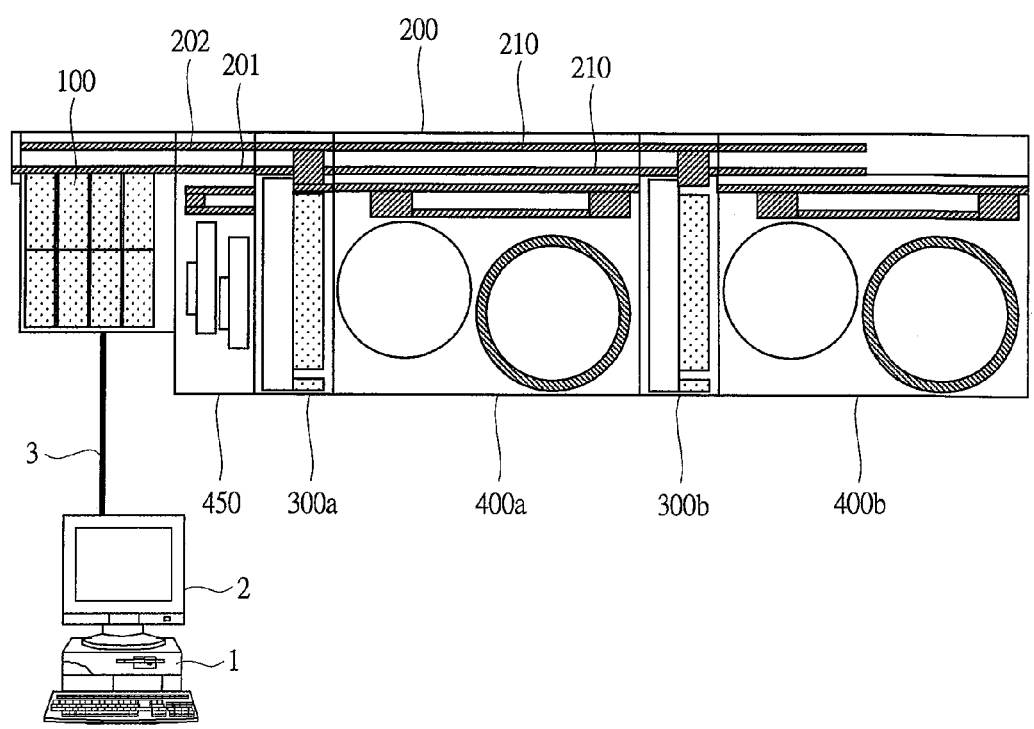

The present invention relates to an automatic analyzing apparatus that performs quantitative and qualitative analyses on a biological sample such as blood and urine, and, more particularly, the present invention relates to an automatic analyzing apparatus in which a rack having a sample container mounted thereon is carried into buffer units adjacently paired with a plurality of analyzing devices, and an appropriate rack in accordance with an analyzing state is selected and carried into an analyzing device.

BACKGROUND ART

Patent Document 1, Patent Document 2, Patent Document 3, etc. describe an automatic analyzing apparatus having a mode in which an analyzing section and a standby section are connected to a main carrying device. Patent Document 1 describes an automatic analyzing apparatus including standby sections on both sides of a reciprocable carrying line, in which a carried-in rack is waited in a standby state at a front standby section as a dispense-waiting rack, and is subjected to a dispensing process at an analyzing section, and then, is waited in a standby state at a back standby section as a reexamination-waiting rack. Patent Document 2 describes an automatic analyzing apparatus including one standby section for a plurality of analyzing sections, in which a rack is carried into the standby section once if a frequency of carrying the rack in exceeds a processing performance of the analyzing section, and the rack in the standby state is carried into the analyzing section after congestion of the analyzing section is solved.

Patent Document 3 describes an automatic analyzing apparatus including buffer units paired with respective processing units, the buffer units being capable of randomly accessing to each of a plurality of racks which are waited in a standby state therein, in which the mutual dependent relationship between a rack carrying unit and an analysis processing unit can be solved by carrying an unprocessed rack into the buffer unit and carrying out the rack from the buffer unit after completion of analyzing processes including an automatic reexamination.

PRIOR ART DOCUMENTS

Patent Documents

Patent Document 1: Japanese Patent Application Laid-Open Publication No. 2004-279357
Patent Document 2: Japanese Patent Application Laid-Open Publication No. 2006-038881
Patent Document 3: Japanese Patent Application Laid-Open Publication No. 2009-150859

DISCLOSURE OF THE INVENTION

Problems to be Solved by the Invention

In a case of structuring an automatic analyzing apparatus in which a plurality of functional modules having different functions and processing performances are connected to each other, if a system for collectively managing all pieces of information is to be achieved, it is too difficult to improve the processing performance as a whole. For example, in a case of an automatic analyzing apparatus configured of two functional modules one of which has a very high processing performance and the other has a very low processing performance, process-waiting specimens are concentrated to the functional module having the low processing performance to cause congestion. Under such a circumstance, there is a risk that, even when a specimen that has to be emergently processed is loaded thereto, the specimen cannot be processed until the congestion is solved.

Moreover, in the system in which the collective management for all pieces of information is achieved, when a new functional module is added thereto since a different analysis is required, it is required to consider influence on the existing functional module or to restructure a carrying plan or others for improving the processing performance as a whole.

Means for Solving the Problem

A buffer unit which is paired with a functional module is connected to a specimen carrying line, and an operating-section computer issues a carrying instruction to the functional module in accordance with each specimen request to perform carrying-in/out operation as managing a carrying-possible state between the respective buffer units and functional modules. That is, by sharing the processes among the units for the carrying function, a system is achieved, in which combination of the plurality of different functional modules is easily made with suppressing the influence on the existing functional module, so that the processing performance as a whole can be improved.

Effects of the Invention

The effect obtained by typical aspects of the present invention disclosed in the present application will be briefly described below.

The effect can provide an automatic analyzing apparatus achieving a rack carrying process such that random carrying access of a specimen rack loaded into a system is possible to a buffer unit connected thereto in accordance with a rack carrying instruction optimized by load calculation of an operating-section computer in consideration of a device state of each of control modules.

BRIEF DESCRIPTIONS OF THE DRAWINGS

Figure 2:
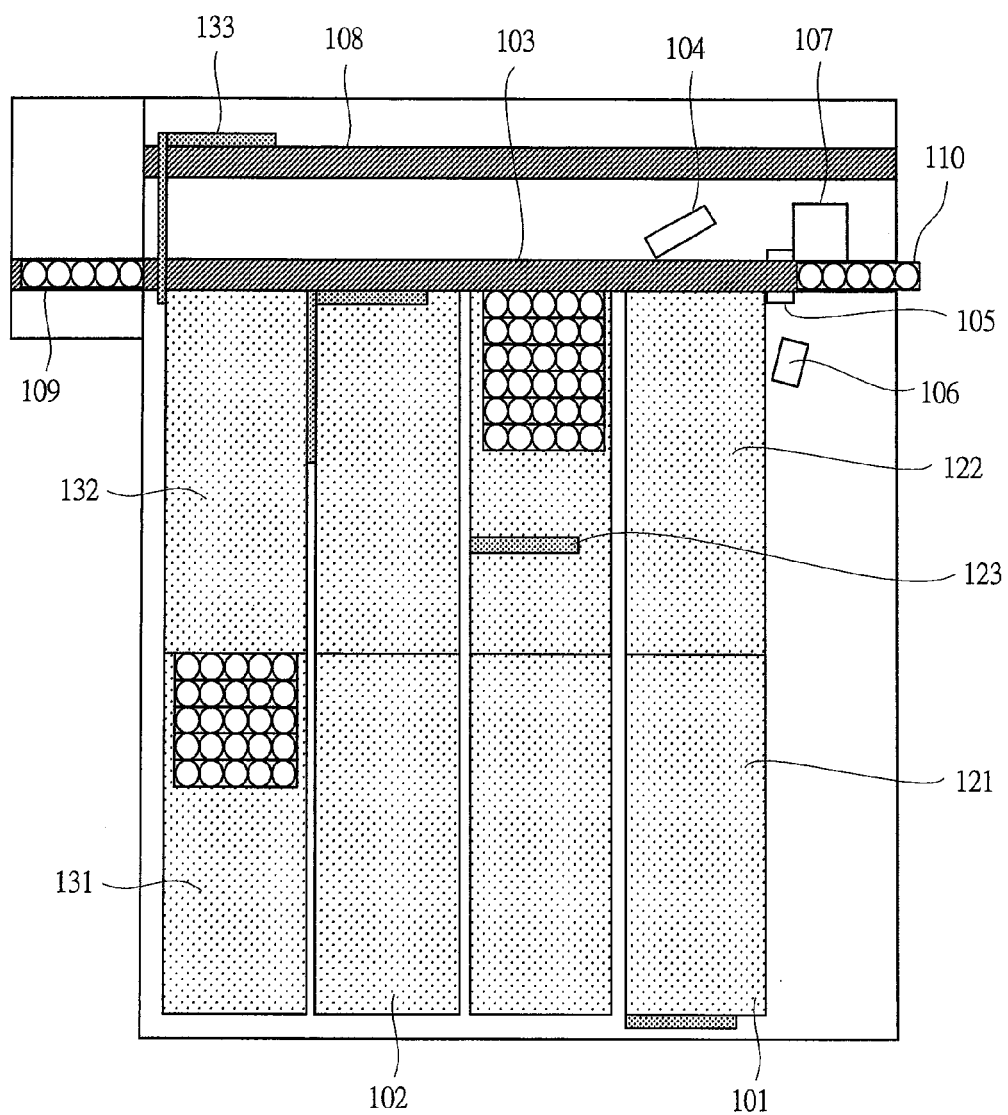
Figure 3:
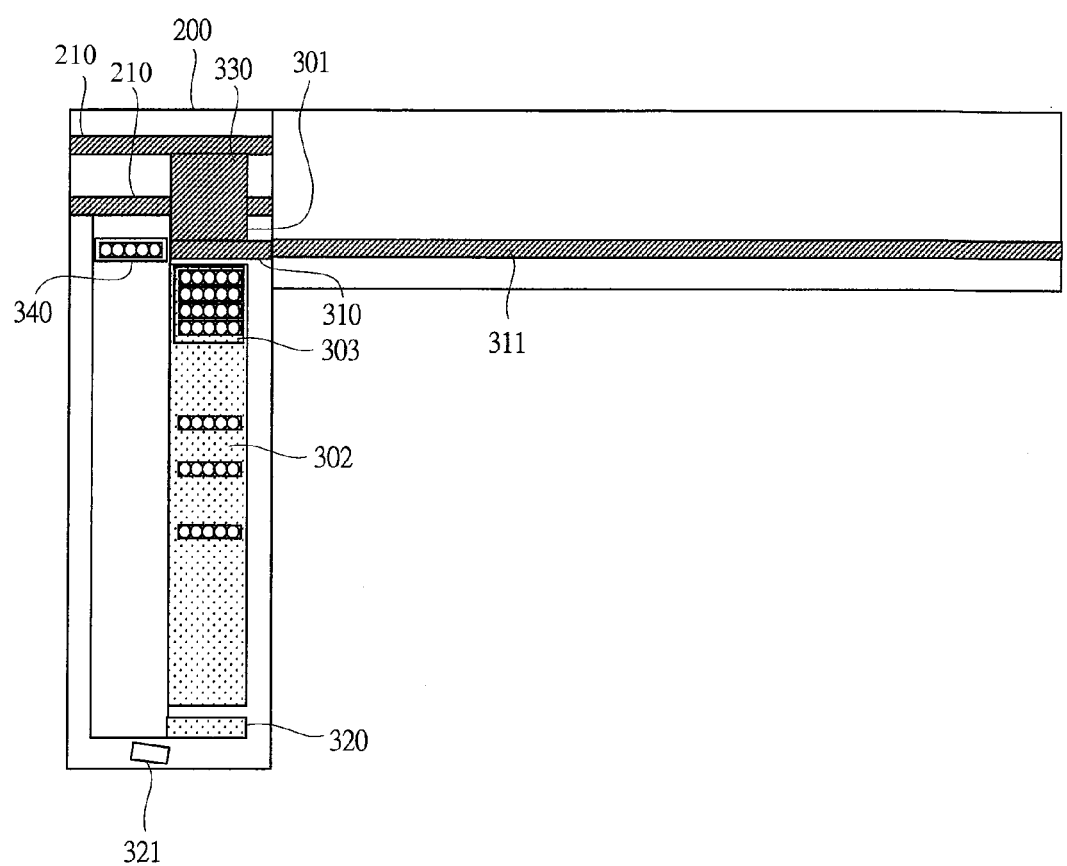
Figure 4:
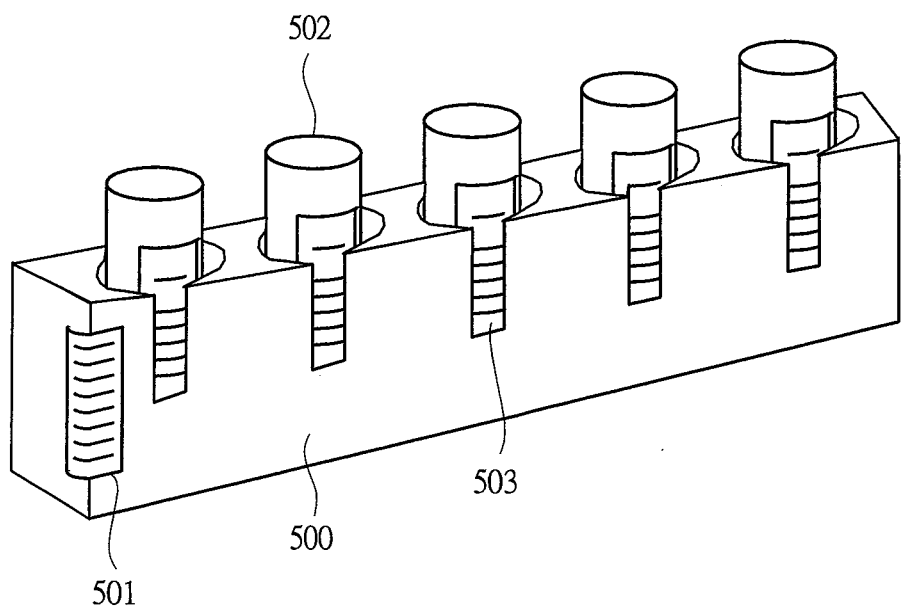
Figure 5:
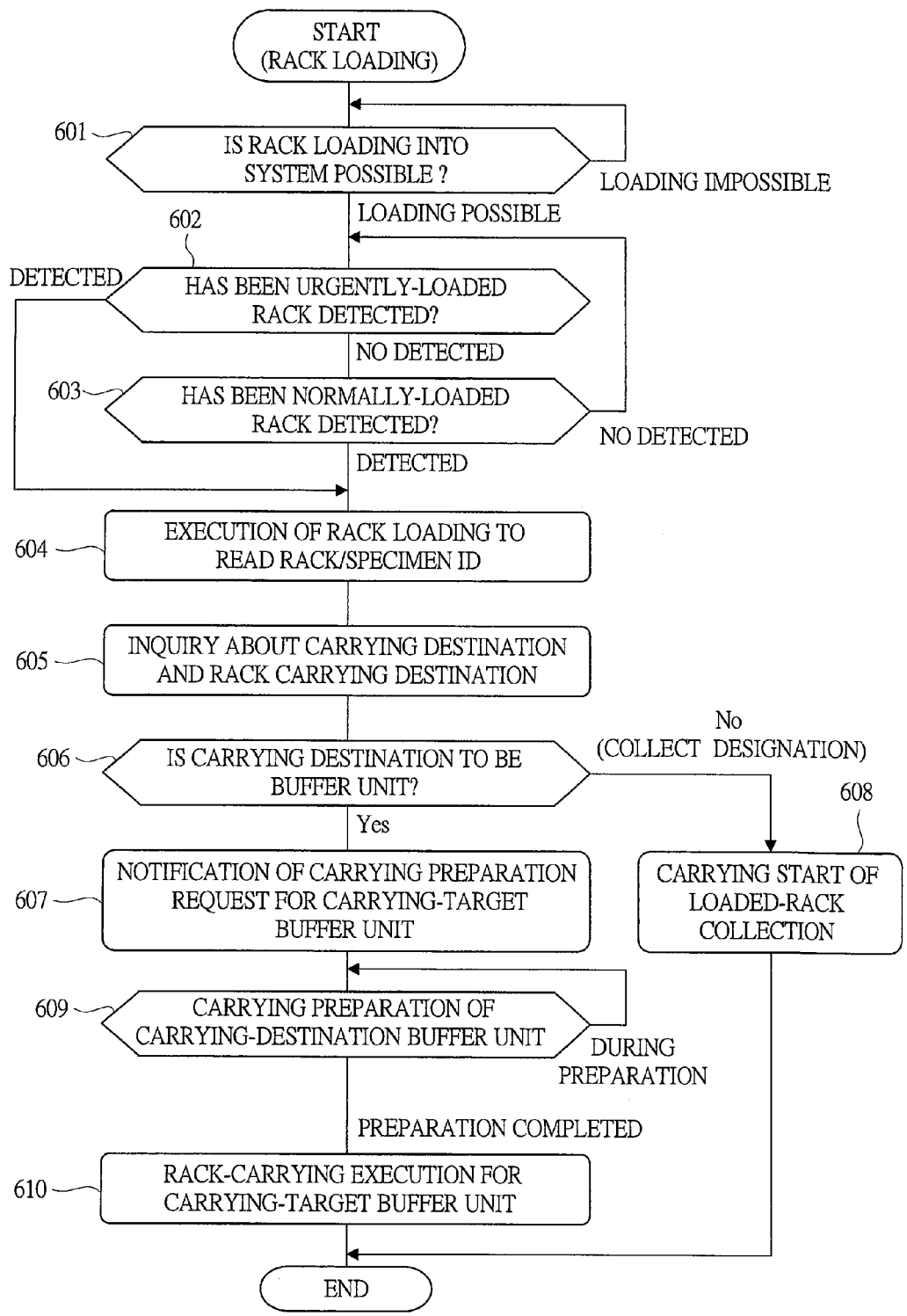
Figure 6:
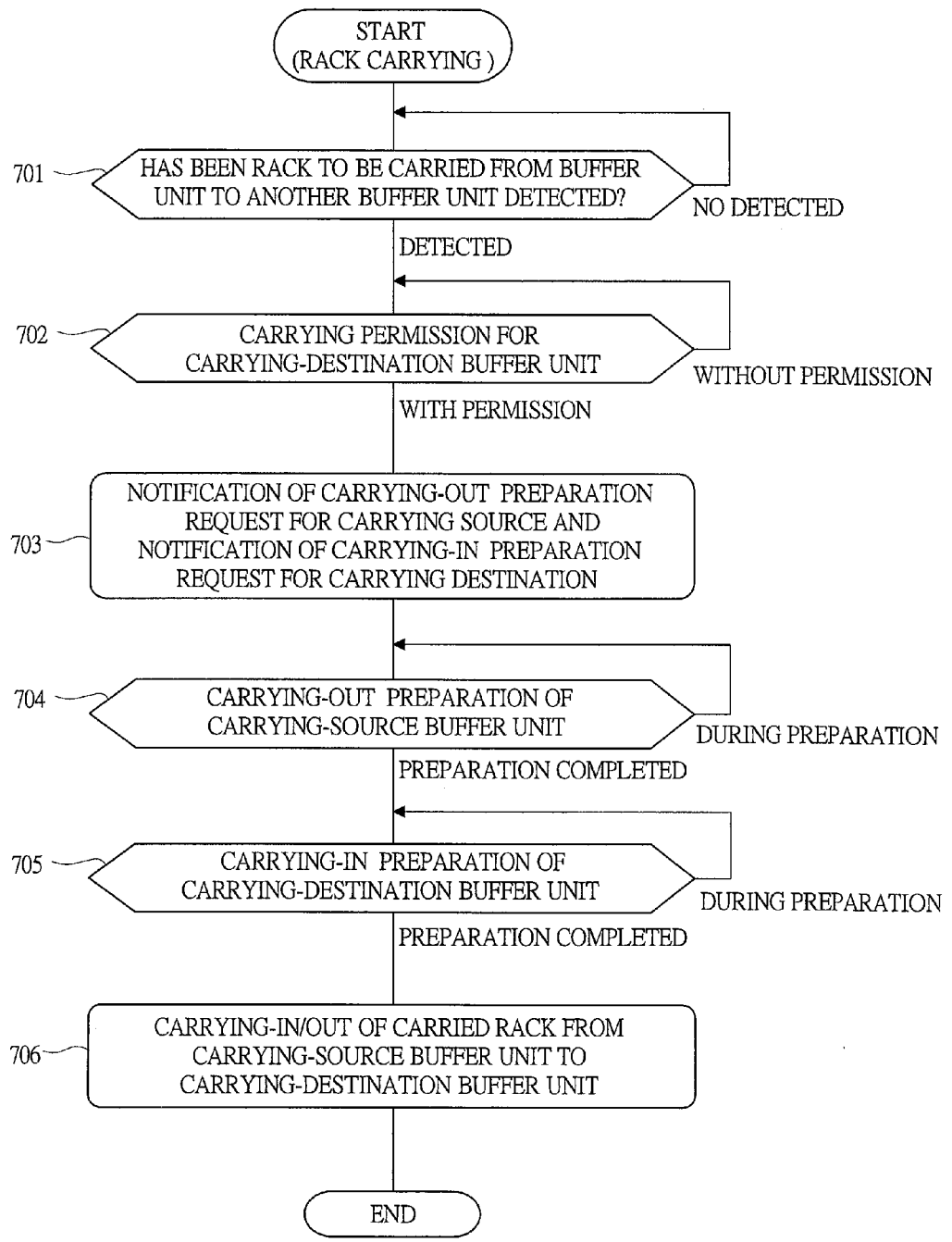
Figure 7:
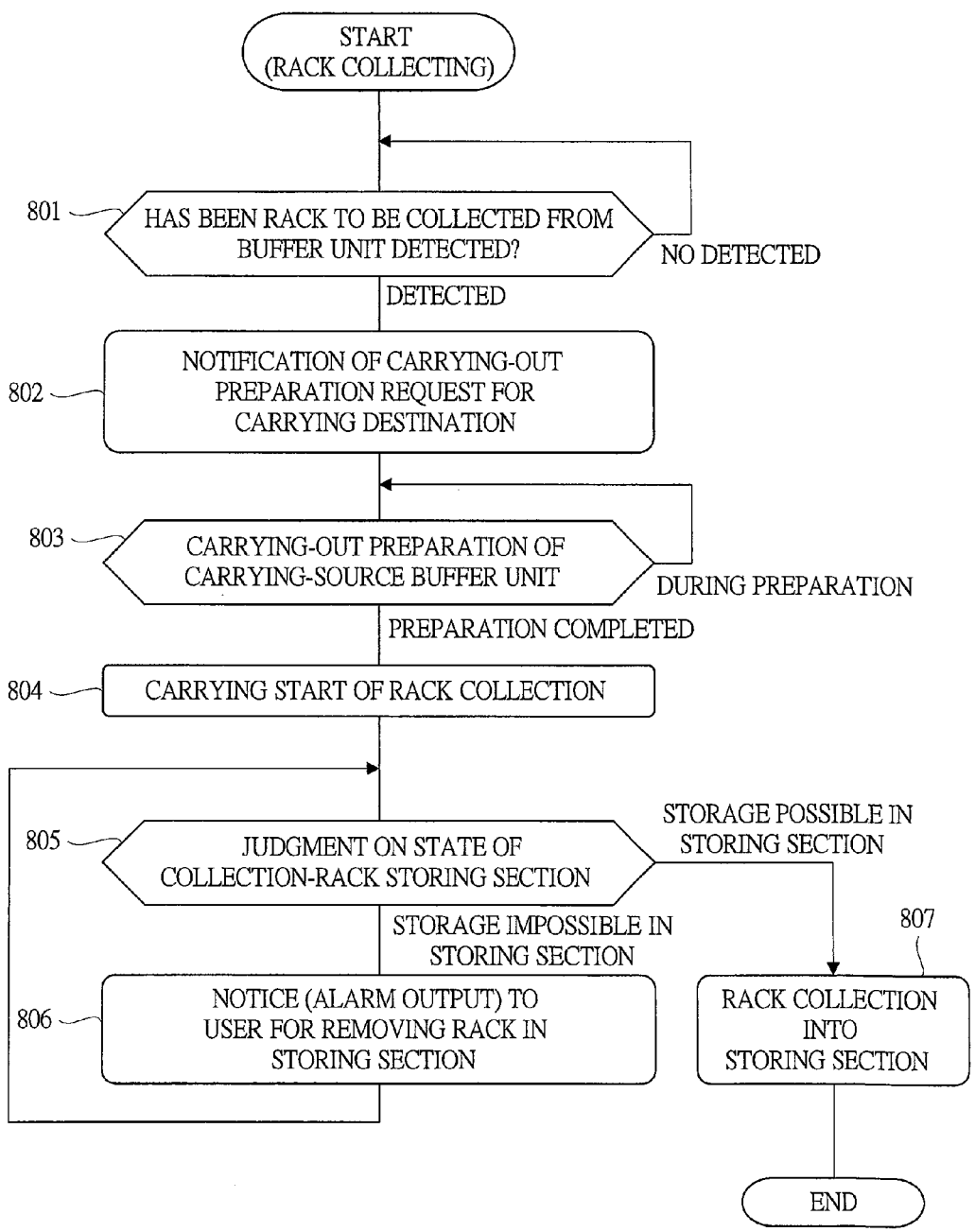
Figure 8:
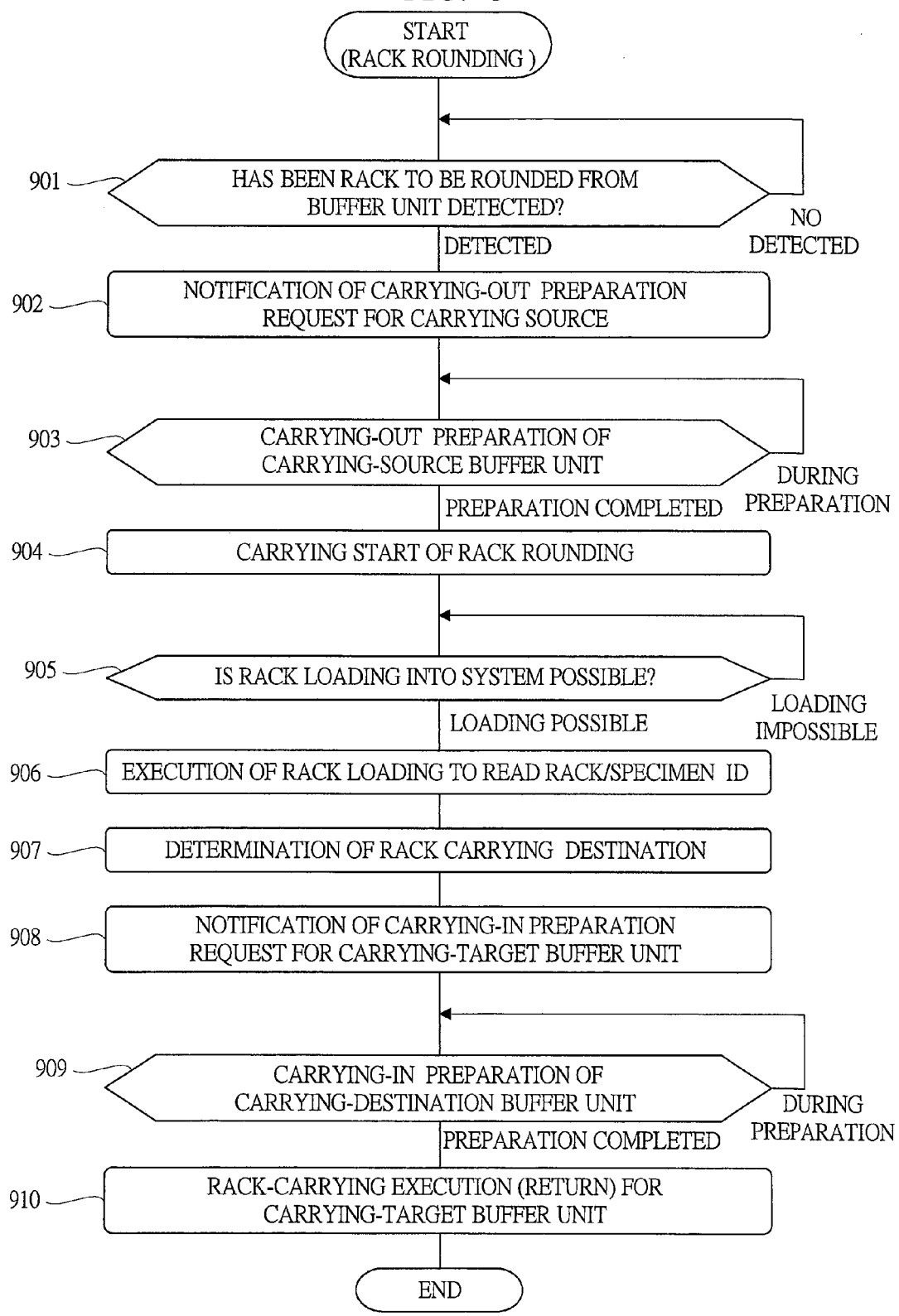
Figure 9:
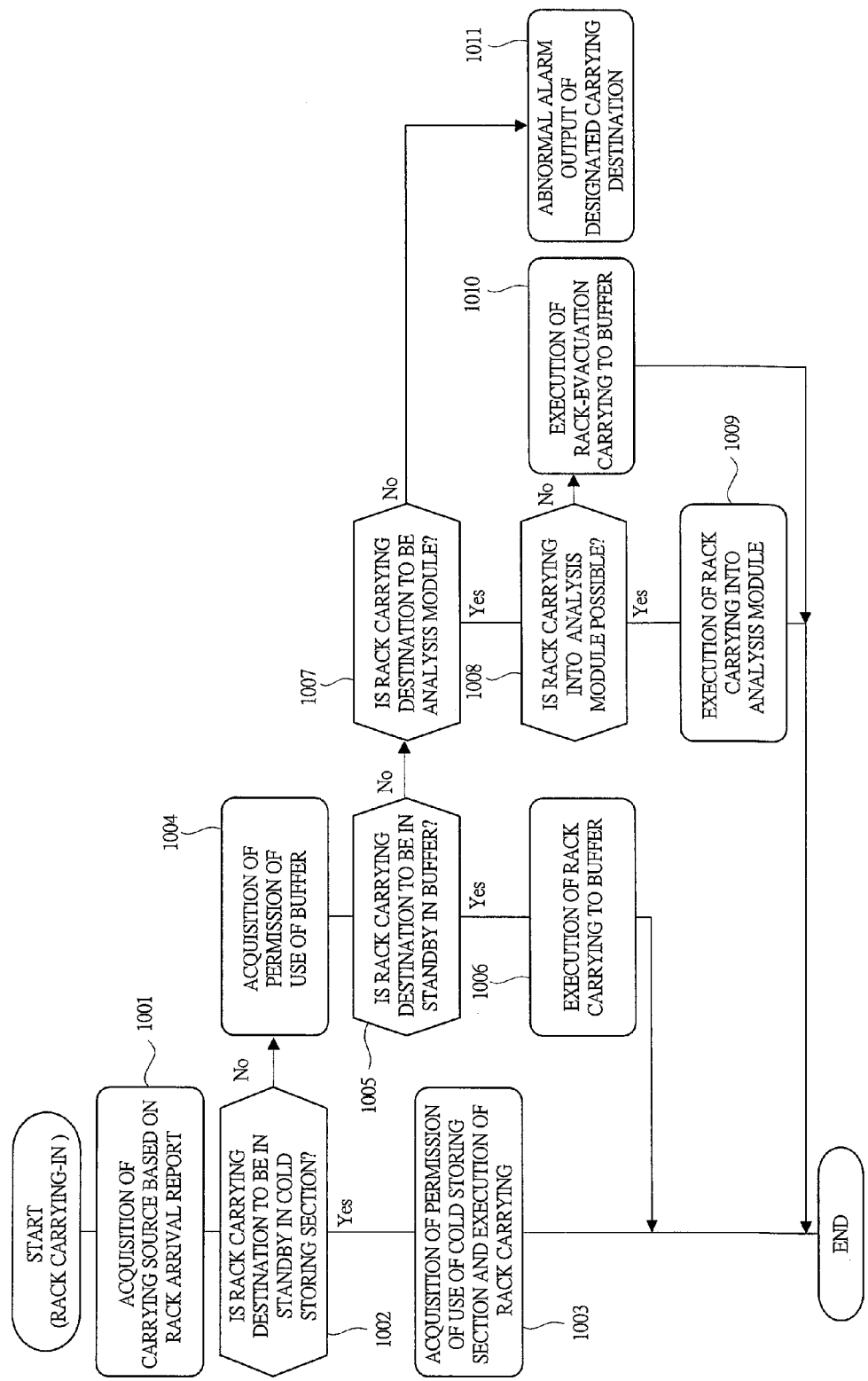
Figure 10:
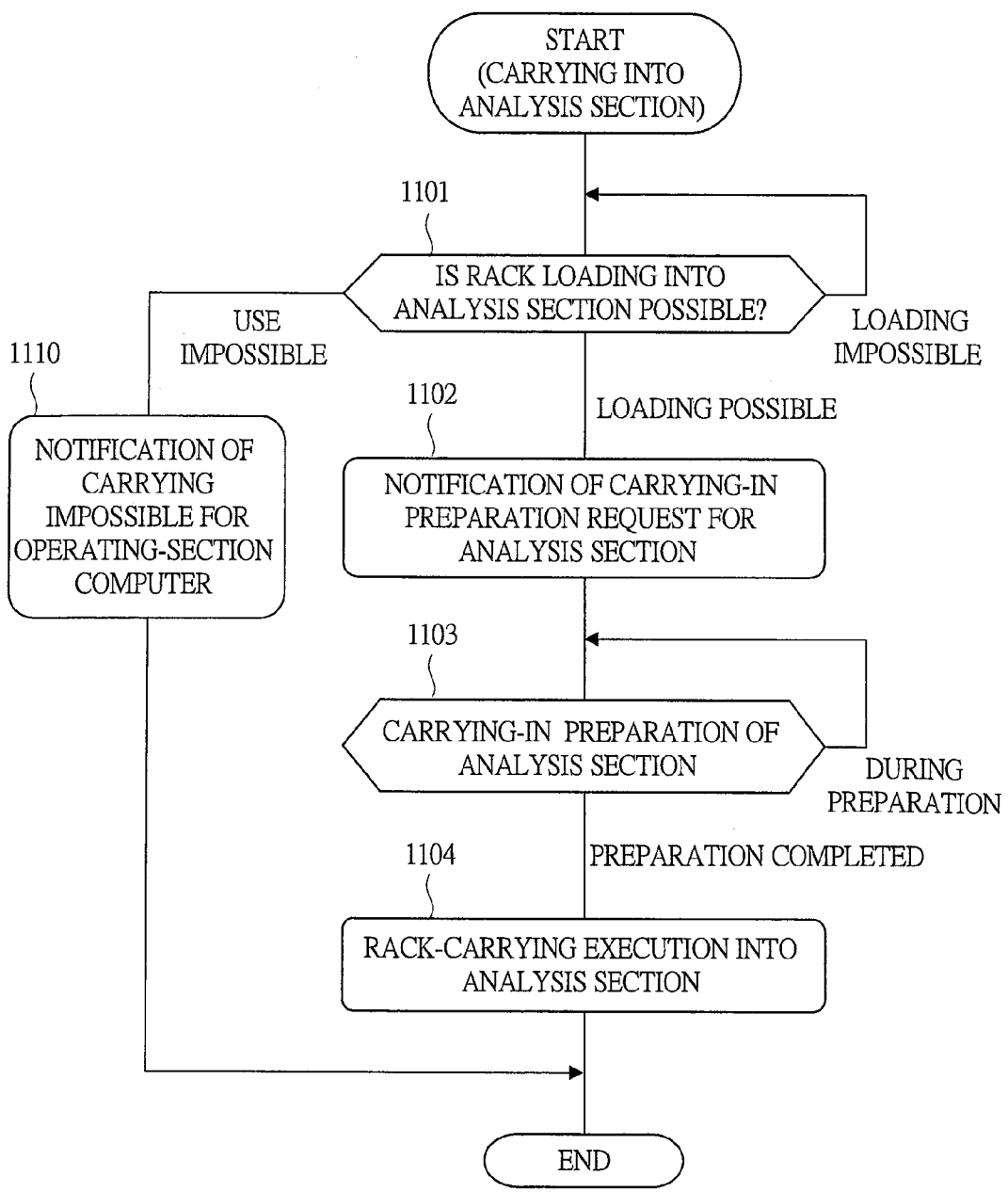
Figure 11:
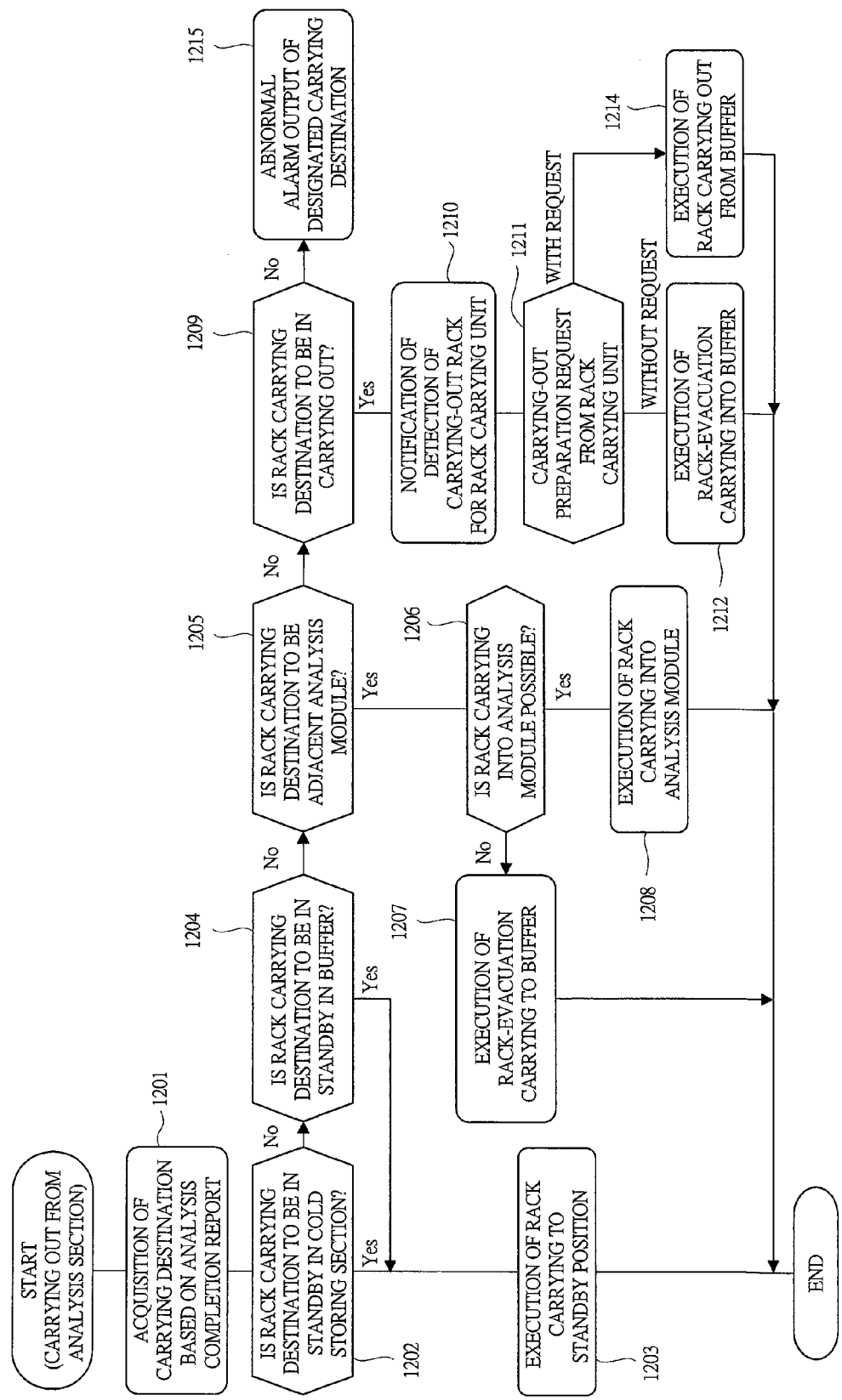
Figure 12:
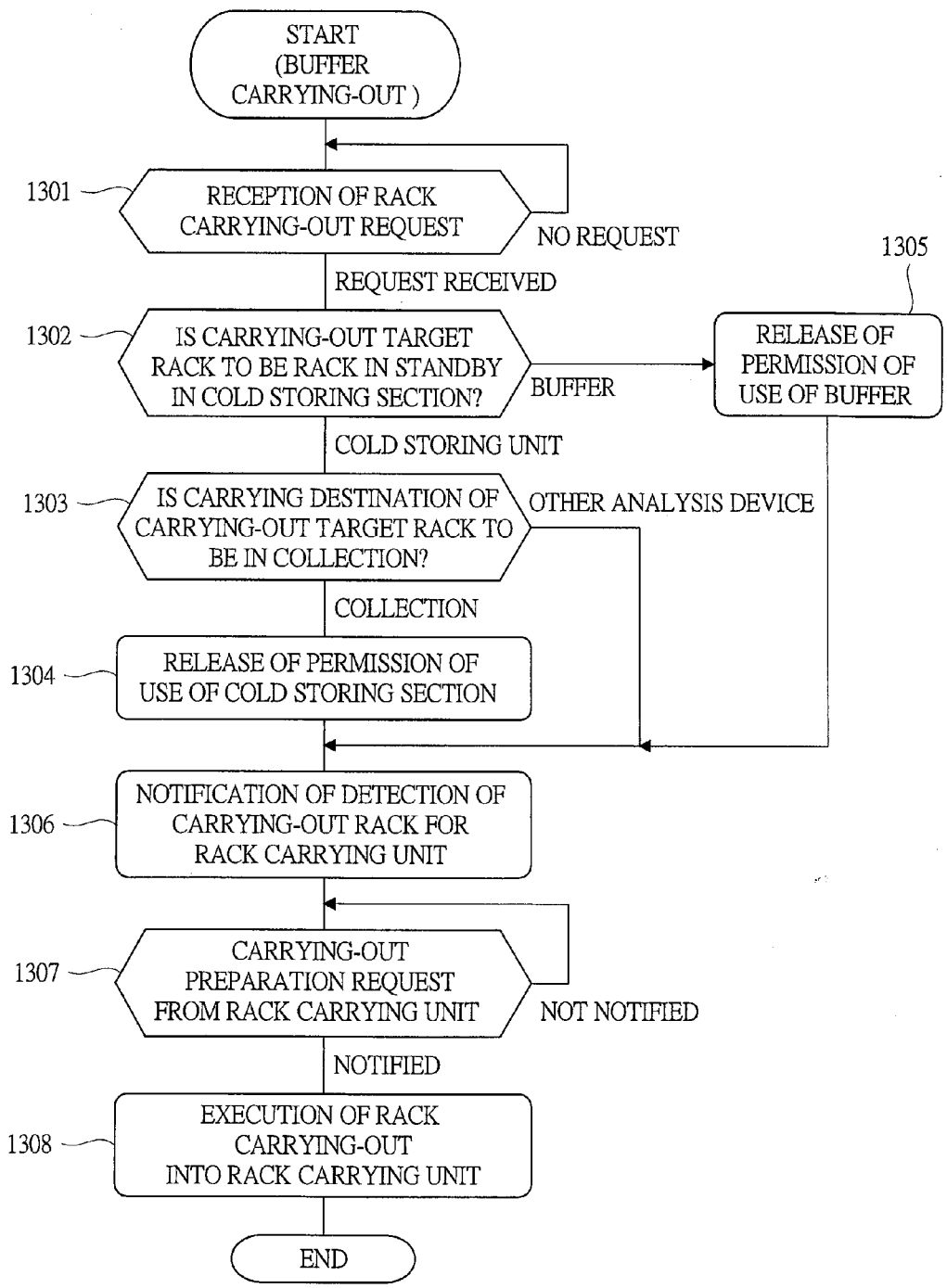

FIG. 1 is a configuration diagram of an automatic analyzing apparatus;
FIG. 2 is a configuration diagram of a sampler unit according to an embodiment of the present invention;
FIG. 3 is a configuration diagram of a buffer unit according to an embodiment of the present invention;
FIG. 4 is a configuration diagram of a specimen rack according to an embodiment of the present invention;
FIG. 5 is a flowchart illustrating a procedure of a rack-load carrying operation;
FIG. 6 is a flowchart illustrating a procedure from a buffer-unit carrying-out operation to a buffer-unit carrying-in operation;
FIG. 7 is a flowchart illustrating a procedure from a buffer-unit carrying-out operation to a rack collecting operation;
FIG. 8 is a flowchart illustrating a procedure from a buffer-unit carrying-out operation to a rack rounding operation;
FIG. 9 is a flowchart illustrating a procedure of a buffer-unit rack carrying-in operation;
FIG. 10 is a flowchart illustrating a procedure of a rack carrying-in operation from a buffer unit into a functional module/additional module;

FIG. 11 is a flowchart illustrating a procedure of a rack carrying operation for a rack carried out from a functional module/additional module into a buffer unit; and FIG. 12 is a flowchart illustrating a procedure of a buffer-unit rack carrying-out operation.

BEST MODE FOR CARRYING OUT THE INVENTION

Hereinafter, with reference to FIGS. 1 to 11, an embodiment of the present invention will be explained below.

FIG. 1 is an entire schematic configuration diagram of an automatic analyzing apparatus according to an embodiment of the present invention.

FIG. 1 illustrates an example of an automatic analyzing apparatus including: a sampler unit 100 to/in which a specimen rack is loaded and stored; a rack carrying unit 200 for carrying the specimen rack between the sampler unit and each functional module; a belt mechanism 210 arranged along the rack carrying unit 200; buffer units 300a and 300b to/from which the specimen rack is transferred from/to the rack carrying unit 200 and in which the specimen rack is temporarily waited in a standby state; functional modules 400a and 400b which are paired with the respective buffer units 300a and 300b and which are arranged on right sides of the respective buffer units; an additional module 450 which is arranged on a left side of the buffer unit 300a; and managing operating-section computers 1 and 2, and a system connected to the operating-section computers via a network 3 is exemplified as the automatic analyzing apparatus.

Next, with reference to FIG. 2, a configuration of the sampler unit 100 will be described.

The sampler unit includes: an loading section 101 for loading the specimen rack into the system; a storing section 102 for collecting the specimen rack from the system; an load-rack moving unit 103 for carrying the specimen rack from the loading section to the rack carrying unit 200; an ID identifying unit 104 for identifying an ID of the specimen rack; a specimen-container-height detecting unit 105 for detecting information of a height of a specimen container provided to the specimen rack; an ID identifying unit 106 for identifying an ID of the specimen container; a rotary mechanism unit 107 for rotating the specimen container in the identification of the ID of the specimen container; a storage-rack moving unit 108 for moving the rack from the rack carrying unit 200 to the storing section 102; an emergent-specimen loading section 109 for loading an emergent specimen rack or a rack from a specimen carrying system connected to an upstream side of the present system; and a rack delivering section 110 from the sampler unit to the rack carrying unit 200.

Next, with reference to FIG. 3, a configuration of the buffer unit 300 will be described.

The buffer unit includes: a rack carrying-in/out standby section 301 in which the specimen rack can be temporarily waited in the standby state in carrying-in/out the specimen rack; a buffer section 302 for temporarily storing the specimen rack inside the buffer unit for initial analysis or reexamination analysis; a cold storing section 303 for storing a precision control specimen, which includes a cold storing mechanism for preventing vaporization of the specimen; a module carrying-in/out standby section 310 used for delivering the rack to/from the functional module; a rack carrying section 311 for carrying the specimen rack to the functional module or carrying the rack out from the functional module; a rack loading section 320 from which the specimen rack can be directly loaded to the buffer unit 300; an ID identifying unit 321 for identifying the ID of the specimen rack loaded from the rack loading section 320 and the ID of the specimen provided to the specimen rack; a specimen-rack transferring mechanism 330 for transferring the specimen rack to/from a belt mechanism 210 arranged along the rack carrying unit 200; and a specimen-rack moving mechanism 340 for moving the specimen rack inside the buffer.

The carrying process of the specimen rack by the rack carrying unit 200 is executed by the carrying instruction from the operating-section computer 1. The carrying instruction to be designated includes to carry the specimen rack from the rack delivering section 110 to the buffer unit 300, to directly collect the rack from the rack delivering section 110, to carry the specimen rack which has been carried out from the buffer unit 300 to another buffer unit 300, to collect the specimen rack which has been carried out from the buffer unit 300, and to round (return) the specimen rack which has been carried out from the buffer unit 300 for application of a maintenance process for the system, and others.

Next, FIG. 4 illustrates an example in which five specimen containers are stored as the specimen rack to be loaded into the present system. However, the number of containers to be storable is not limited to this number but may be one or larger, and the number of ten or larger is usable. A specimen rack 500 used as a supporting body for storing one or more specimen containers 502 has an elongated box shape. On the specimen rack, a label 501 that indicates information (such as a bar code, a number, and a character) for identifying each of the specimen racks is attached. Moreover, on an outer wall of each of the specimen containers 502, a specimen identification label 503 that indicates specimen information containing a specimen receipt number, patient information such as a patient name and age, an inspection item name, and others is labeled.

Next, with reference to FIG. 5, the load carrying process of the specimen rack in the sampler unit 100 and the rack carrying unit 200 inside the present system will be described. Note that a number attached to a sentence end represents a symbol corresponding to each processing step in the flowchart of FIG. 5.

In the present system, after placing a loading tray 121 in which the plurality of specimen racks are provided to the loading section 101, an analyzing process is started by a user's instruction at the operating-section computer 1. However, it is not allowed to load the specimen rack into the system before all states of the devices including the rack carrying unit 200, the plurality of buffer units 300 connected to the rack carrying unit, and the functional module transit to an analyzable state. Moreover, the number of specimen racks which can be simultaneously loaded into the system is unambiguously defined although it is different depending on the system configuration and the designated information at the operating-section computer, and therefore, such a number of additional load as exceeding the total number of the loaded specimen racks is not allowed (step 601).

After all states of the devices transit to the analyzable state, movement of a specimen rack, which is provided to the loading tray 121, to an loading buffer section 122 by the sampler unit 100 is started. When all the specimen racks provided to the loading tray 121 are moved to the loading buffer section 122, it is allowed to exchange the loading tray 121. Therefore, if a loading tray 121 to which a specimen rack has been provided is newly set by the user, the additional load of the specimen rack into the system can be supported.

The specimen rack moved to the rack loading buffer section 122 is detected (step 603). If the specimen rack is detected, the specimen rack is carried by the load-rack moving unit 103, ID information of the rack and the specimen provided thereto is read (step 604), and a carrying destination of the corresponding rack is inquired of the operating-section computer 1. The operating-section computer 1 which has received the inquiry notifies the rack carrying unit 200 of the optimized carrying destination of the corresponding rack. The rack carrying unit 200 determines the carrying destination of the corresponding rack based on the designation of the notified carrying destination of the specimen rack (step 605).

At this time, if a specimen rack placed in the emergent-specimen loading section 109 is detected, the carrying operation of the specimen rack placed in the emergent-specimen loading section 109 is prioritized (step 602).

However, if a specimen rack which has been previously loaded by the rack loading buffer section 122 is any of grouped specimen racks in which the precision control specimen has been stored or in which a calibrator specimen has been stored, the load by the rack loading buffer section 122 is prioritized as long as the grouped racks continue.

As a carrying destination of a specimen rack to be initially supplied into the system, there are cases that the functional module 400 adjacent to the specific buffer unit 300 is specified and that a carrying passage used for direct collection is specified because the read ID information is unspecific (step 606). In the case that the rack is carried to the specific buffer unit 300, the buffer unit 300 to be the carrying-in destination is notified of a belt mechanism 210 to be used for carrying the specimen rack and ID information capable of specifying the rack to be carried in, as a rack carrying-in preparation request (step 607). This is for carrying the corresponding rack into the buffer unit by using the specimen-rack transferring mechanism 330 of the buffer unit when the rack carrying unit 200 carries the corresponding rack to the buffer unit by using the belt mechanism 210.

Based on the movement of the specimen-rack transferring mechanism 330 of the buffer unit 300 onto the belt mechanism 210 as the carrying-in preparation operation, the buffer unit 300 reports completion of the carrying-in preparation of the corresponding rack to the rack carrying unit 200. When the rack carrying unit 200 receives the report of the completion of the carrying-in preparation from the buffer unit 300 (step 609), the specimen rack is carried by the belt mechanism 210 to a position of the specimen-rack transferring mechanism 330 of the buffer unit 300 which is to be a carrying-in target of the corresponding rack, and the rack is carried in the buffer unit 300 (step 610).

Also in the case that the corresponding rack is directly collected, the specimen-rack transferring mechanism 330 of the buffer unit 300 is utilized (step 608). In this case, by the rack carrying unit 200, it is determined which buffer unit 300 is selected from the plurality of buffer units 300 which are connected onto the system based on judgment on the operation states of the devices.

Next, with reference to FIG. 6, a carrying process of a specimen rack will be described, the carrying process being used for carrying the specimen rack which has been carried out from the buffer unit 300 to another buffer unit 300 in order to analyze it by using another functional module 400.

The specimen rack which has been carried to the buffer unit 300 once is stored in the buffer unit 300 until it is subjected to the analysis by the functional module 400. Based on completion of the analyzing process, the operating-section computer 1 notifies the rack carrying unit 200 and the buffer unit 300 of the carrying destination of the corresponding rack.

When the corresponding rack is in a carrying-out possible state, the buffer unit 300 notifies the rack carrying unit 200 of the ID information capable of specifying the corresponding rack and the fact that the specimen rack to be the carrying-out target has been detected.

The rack carrying unit 200 specifies the carrying destination of the specimen rack to be carried out from the buffer unit 300 based on the carrying designation information of the specimen rack which has been previously notified from the operating-section computer 1 and the ID information capable of specifying the corresponding rack which has been notified from the buffer unit 300 (step 701). At this time, the belt mechanism 210 to be used for carrying the specimen rack is selected simultaneously.

The rack carrying unit 200 judges a usage state of the buffer unit 300 which is the carrying destination of the corresponding rack (step 702), and, if it is judged that the carrying is possible, the rack carrying unit notifies the buffer unit 300, which is a carrying-out source, of a belt mechanism 210 to be used for carrying the specimen rack and ID information capable of specifying the rack to be carried out, as a rack carrying-out preparation request. Simultaneously, the rack carrying unit notifies the buffer unit 300, which is a carrying-in destination, of a belt mechanism 210 to be used for carrying the specimen rack and ID information capable of specifying the rack to be carried in, as a rack carrying-in preparation request (step 703).

Based on the movement of the specimen-rack transferring mechanism 330 of the buffer unit 300 onto the belt mechanism 210 as the carrying-out preparation operation, the buffer unit 300 from which the specimen rack is carried out reports completion of the carrying-out preparation of the corresponding rack to the rack carrying unit 200 (step 704). Also, based on the movement of the specimen-rack transferring mechanism 330 of the buffer unit 300 onto the belt mechanism 210 as the carrying-in preparation operation, the buffer unit 300 in which the specimen rack is carried reports completion of the carrying-in preparation of the corresponding rack to the rack carrying unit 200 (step 705).

When the rack carrying unit 200 receives the report of the completion of the carrying-out preparation from the carrying-out-source buffer unit 300 and the report of the completion of the carrying-in preparation from the carrying-in-destination buffer unit 300, the specimen rack is carried by the belt mechanism 210 from a position of the specimen-rack transferring mechanism 330 of the carrying-out-source buffer unit 300 to a position of the specimen-rack transferring mechanism 330 of the buffer unit 300 which is to be a carrying-in target of the corresponding rack, and the specimen rack which has reached the carrying-in-destination buffer unit 300 is carried therein (step 706).

Next, with reference to FIG. 7, a carrying process of a specimen rack will be described, the carrying process being used for collecting and carrying the specimen rack which has been carried out from the buffer unit 300. Note that a storing section 102 is configured of a storing buffer section 132 and a storing tray 131 provided to the storing section 102. The storing tray 131 is provided thereto and used by the user in order to take the collected specimen rack out from the apparatus. The collected specimen rack, which has been carried in front of the storing section 102 by the storage-rack moving unit 108, is drawn into the storing buffer section 132 by a storing lever 133. At this time, if the storing tray 131 is not full, it is further moved to the storing tray 131 by the storing lever 133.

Based on the judgment that all the analyzing operations for the specimen rack existing inside the buffer unit 300 have been completed, the operating-section computer 1 instructs the rack carrying unit 200 and the buffer unit 300 to collect and carry the corresponding rack.

When the corresponding rack is in a carrying-out possible state, the buffer unit 300 notifies the rack carrying unit 200 of ID information capable of specifying the corresponding rack and the fact that the specimen rack to be the carrying-out target has been detected.

The rack carrying unit 200 specifies the carrying destination of the specimen rack to be carried out from the buffer unit 300 based on the carrying designation information of the specimen rack which has been previously notified from the operating-section computer 1 and the ID information capable of specifying the corresponding rack which has been notified from the buffer unit 300 (step 801). At this time, the belt mechanism 210 to be used for carrying the specimen rack is selected simultaneously.

The rack carrying unit 200 notifies the buffer unit 300, which is a carrying-out source, of a belt mechanism 210 to be used for carrying the specimen rack and ID information capable of specifying the rack to be carried out, as a rack carrying-out preparation request (step 802).

Based on the movement of the specimen-rack transferring mechanism 330 of the buffer unit 300 onto the belt mechanism 210 as the carrying-out preparation operation, the buffer unit 300 from which the specimen rack is carried out reports completion of the carrying-out preparation of the corresponding rack to the rack carrying unit 200 (step 803). When the rack carrying unit 200 receives the report of the completion of the carrying-out preparation from the carrying-out-source buffer unit 300, the specimen rack is carried by the belt mechanism 210 from the position of the specimen-rack transferring mechanism 330 of the carrying-out-source buffer unit 300 to a delivery position of the storage-rack moving unit 108 (step 804).

At the time when the specimen rack has been carried to the delivery position of the storage-rack moving unit 108, it is confirmed that the collected rack exists on the storing section 102 (step 805), and, if the storing section 102 is already full and is in a rack-collection impossible state, an alarm for a request of exchange of the storing tray 131 provided to the storing section 102 is outputted to the user (step 806). This alarm is periodically outputted until the exchange of the storing tray 131 is completed. Since a space capable of storing the specimen rack can be provided in the storing section 102 by the exchange of the storing tray 131, the specimen rack is collected into the storing section 102 (step 807).

Next, with reference to FIG. 8, a carrying process of a specimen rack will be described, the carrying process being used for rounding and carrying the specimen rack which has been carried out from the buffer unit 300. This specimen-rack carrying process is a carrying operation used for supporting a maintenance process for the system, and transfers the specimen rack, which has been carried in front of the storing section 102 by the storage-rack moving unit 108, to the load-rack moving unit 103 by the storing lever 133 to carry the rack into the system again.

Based on the judgment that all the maintenance operations for the specimen rack existing inside the buffer unit 300 have been completed, the operating-section computer 1 instructs the rack carrying unit 200 and the buffer unit 300 to round and carry the corresponding rack.

When the corresponding rack is in a carrying-out possible state, the buffer unit 300 notifies the rack carrying unit 200 of ID information capable of specifying the corresponding rack and the fact that the specimen rack to be the carrying-out target has been detected.

The rack carrying unit 200 specifies the carrying destination of the specimen rack to be carried out from the buffer unit 300 based on the carrying designation information of the specimen rack which has been previously notified from the operating-section computer 1 and the ID information capable of specifying the corresponding rack which has been notified from the buffer unit 300 (step 901). At this time, the belt mechanism 210 to be used for carrying the specimen rack is selected simultaneously.

The rack carrying unit 200 notifies the buffer unit 300, which is a carrying-out source, of a belt mechanism 210 to be used for carrying the specimen rack and ID information capable of specifying the rack to be carried out, as a rack carrying-out preparation request (step 902).

Based on the movement of the specimen-rack transferring mechanism 330 of the buffer unit 300 onto the belt mechanism 210 as the carrying-out preparation operation, the buffer unit 300 from which the specimen rack is carried out reports completion of the carrying-out preparation of the corresponding rack to the rack carrying unit 200 (step 903). When the rack carrying unit 200 receives the report of the completion of the carrying-out preparation from the carrying-out-source buffer unit 300, the specimen rack is carried by the belt mechanism 210 from the position of the specimen-rack transferring mechanism 330 of the carrying-out-source buffer unit 300 to a delivery position of the storage-rack moving unit 108 (step 904).

At the time when the specimen rack has been carried to the delivery position of the storage-rack moving unit 108, it is confirmed that no specimen rack exists on the load-rack moving unit 103 (step 905), the specimen rack which has been carried in front of the storing section 102 by the storage-rack moving unit 108 is transferred to the load-rack moving unit 103 by the storing lever 133 to be carried to read ID information of the rack and the provided specimen (step 906), and the carrying destination of the corresponding rack is inquired of the operating-section computer 1. The operating-section computer 1 which has received the inquiry notifies the rack carrying unit 200 of the carrying destination of the corresponding rack for the maintenance operation. Based on the notified designation of the carrying destination of the specimen rack, the rack carrying unit 200 determines the carrying destination of the corresponding rack (step 907).

Because of the maintenance operation, the carrying destination is the buffer unit 300. The rack carrying unit 200 notifies the buffer unit 300, which is a carrying-in destination, of a belt mechanism 210 to be used for carrying the specimen rack and ID information capable of specifying the rack to be carried in, as a rack carrying-in preparation request (step 908).

Based on the movement of the specimen-rack transferring mechanism 330 of the buffer unit 300 onto the belt mechanism 210 as the carrying-in preparation operation, the buffer unit 300 reports completion of the carrying-in preparation of the corresponding rack to the rack carrying unit 200. When the rack carrying unit 200 receives the report of the completion of the carrying-in preparation from the buffer unit 300 (step 909), the specimen rack is carried by the belt mechanism 210 to a position of the specimen-rack transferring mechanism 330 of the buffer unit 300 which is to be a carrying target of the corresponding rack, and the specimen rack is carried into the buffer unit 300 (step 910).

In the carrying process of the specimen rack by the rack carrying unit 200, if the supplying operation of the specimen rack is continued in a state that the plurality of specimen racks are carried into the system, the request to the buffer unit 300 for the specimen-rack carrying-in operation of a specimen rack to be newly loaded into the system overlap with the request from this buffer unit 300 for the specimen-rack carrying-out operation or others. Moreover, if this mechanism is operated in a state that the plurality of specimen racks exist on one belt mechanism 210, there is a possibility that the specimen racks interfere with the specimen-rack moving mechanism 340 of the buffer unit 300 that is executing the carrying-in operation and the carrying-out operation to and from the rack carrying unit 200. In such a case, a carrying control logic for controlling the carrying process is adopted, in which the rack carrying unit 200 performs a source management of this mechanism to lock the source when a carrying process of one specimen rack starts and release the source when the carrying process is completed so that the plurality of specimen racks do not simultaneously exist therein.

When the specimen rack is carried among the plurality of buffer units 300 connected to this unit, the carrying operation starts after judging a start-possible state for the carrying operation of this unit, and therefore, a carrying control logic is adopted in the rack carrying unit 200, the carrying control logic executing the carrying operation so that the carrying-in/out operations of the buffer unit 300 are always synchronized with the carrying operation of this unit.

When the specimen rack is carried among the plurality of buffer units 300 connected to this unit, the specimen-rack carrying process is not established unless the control is made in synchronization of securement of all the sources for the carrying-out-source buffer unit 300, the carrying-in-destination buffer unit 300, and the belt mechanism 210 with each other, and therefore, a carrying control logic is adopted in the rack carrying unit 200, the carrying control logic being capable of judging whether any other carrying-possible specimen rack exists or not if a carrying condition is not established for some reason, and, if any carrying-start-possible specimen rack is detected, previously executing the carrying process of the detected rack.

Moreover, when the specimen rack to be the carrying target is always detected at the same carrying position, a case that it is difficult to start the carrying process of the specimen rack occurs. In order to avoid the carrying problem described above, a carrying control logic may be adopted in the rack carrying unit 200, the carrying control logic putting a priority order on the selection of the carrying start position so as to lower the priority order of the carrying process start from the carrying position at which the carrying process of the specimen rack has been already started.

In the present embodiment, the carrying process of the specimen rack by the buffer unit 300 is executed by the carrying instruction from the operating-section computer 1. As the designated carrying instruction for the specimen rack which has been carried from the rack carrying unit 200, the carrying to the functional module 400, the carrying to the additional module 450, the carrying to the cold storing section 303, and the carrying to the buffer section 302 are instructed. Moreover, for the specimen rack which has been carried into the functional module 400 or the additional module 450, and has been subjected to the analysis, and then, has been carried out from this module, the carrying to another adjacent module 400 or 450, the carrying to the cold storing section 303, the carrying to the buffer section 302, the carrying to the rack carrying unit 200 for carrying the rack to another buffer unit 300, the carrying to the rack carrying unit 200 for the collection and others are instructed.

Next, with reference to FIG. 10, the carrying-in process of the specimen rack from the buffer unit 300 to the functional module 400 and the additional module 450 will be described.

In the functional module 400 and the additional module 450, the number of specimen racks which can be carried in these modules is defined. When the defined number of specimen racks has already been carried therein, no specimen rack can be carried therein from the buffer unit 300. Moreover, since there is a case that these modules cannot be used for some reason such as lack of a reagent to be used therein, a carrying control logic is adopted in the buffer unit 300, the carrying control logic performing a process (step 1101) of judging whether the carrying-in process is possible or not prior to the carrying of the specimen rack to these modules.

The adopted control logic is as follows. If the number of specimen racks which can be carried in the functional module 400 or the additional module 450 has already been carried therein, it is only have to stop the start of the carrying-in operation until the specimen rack is carried out from the module. However, if these modules are unavailable for some reason, the operating-section computer 1 is notified (step 1110) of the fact that the instructed carrying of the specimen rack is impossible, so that the designated carrying destination of this specimen rack is inquired.

When the specimen rack is carried from the buffer unit 300 into the functional module 400, this module is notified of ID information capable of specifying the specimen rack as a rack carrying-in preparation request (step 1102).

When the carrying-in preparation of the specimen rack in the functional module 400 is completed, this module notifies the buffer unit 300 of the report of the completion of the carrying-in preparation, so that the specimen rack which is waited in the standby state in the rack carrying-in/out standby section 301, the cold storing section 303, or the buffer section 302 is carried to the module carrying-in/out standby section 310 by the specimen-rack moving mechanism 340, and the specimen rack is carried to this module by the rack carrying section 311 to perform the carrying-in operation of the specimen rack (step 1104).

When a specimen rack is carried from the buffer unit 300 into the additional module 450, the specimen rack which is waited in the standby state in the rack carrying-in/out standby section 301, the cold storing section 303, or the buffer section 302 is carried to the module carrying-in/out standby section 310 by the specimen-rack moving mechanism 340, and the specimen rack is directly carried in this module.

Next, a judgment logic used when the specimen rack inside the buffer unit is carried into an adjacent functional module will be described. In the buffer unit, it is judged whether or not the adjacent functional module/additional module in which the specimen rack is to be carried is in the analysis-possible state, and, if the judgment is made as an operable state, the carrying-in/out operation of the specimen rack in the corresponding functional module/additional module starts.

Moreover, in the buffer unit, it is judged whether or not there is a space which can store the specimen rack inside the adjacent functional module/additional module in which the specimen rack is to be carried so that a reception preparation of the functional module side is ready (so that there is a vacant position in the functional module), and, if the judgment is made as the operable state, the carrying-in/out operation of the specimen rack in the corresponding functional module/additional module starts.

Further, in the buffer unit, it is judged whether or not a specimen-rack carrying-in/out operation (for example, the delivery of the specimen rack which has already been carried out from the functional module/additional module, the specimen-rack carrying-in/out operation with the rack carrying unit, or others) has not been started yet except for the specimen-rack carrying-in operation into the adjacent functional module/additional module in which the specimen rack is to be carried, and, if the judgment is made as the operable state, the carrying-in operation of the specimen rack into the corresponding functional module/additional module starts.

The specimen rack for which the process in the functional module/additional module has been ended is carried out toward the buffer unit. It is confirmed that another specimen-rack carrying operation (the carrying-in/out operation to/from the rack carrying unit or others) has not been started yet in the buffer unit, and, if the judgment is made as the operable state, the carrying-out operation of the specimen rack from the corresponding functional module/additional module into the buffer unit starts.

Next, with reference to FIG. 11, the carrying process of the specimen rack which has been carried out from the functional module 400 or the additional module 450 to the buffer unit 300 will be described.

When the buffer unit 300 receives the specimen rack from the functional module 400 or the additional module 450, the buffer unit simultaneously receives the ID information capable of specifying the rack to be carried out from these modules.

When the reception of the specimen rack is completed, the operating-section computer 1 is notified of the ID information capable of specifying the rack which has been carried out from the functional module 400 or the additional module 450 to be informed of the completion of the analysis for the specimen rack, so that the carrying destination of this specimen rack is acquired from the operating-section computer 1 (step 1201).

In order to avoid a state that the specimen rack remains in the module carrying-in/out standby section 310, a carrying control logic is adopted in the buffer unit 300, the carrying control logic carrying to evacuate the specimen rack once to the cold storing section 303 or the buffer section 302 which has acquired the permission of use if it is judged that the specimen rack cannot be directly carried to the designated carrying destination (steps 1206 and 1211), and, after the state of the target specimen rack transits to the carrying-possible state to the designated carrying destination, carrying the evacuated specimen rack thereto (steps 1207 and 1212).

When there is the specimen rack which needs to be analyzed in the functional module or the additional module adjacent to each of the plurality of buffer units existing inside the system, the carrying is impossible sometimes because there is no vacancy in the buffer section inside the buffer unit to be the carrying destination target, which results in difficulty of the carrying of the specimen rack in the entire system.

In such a case, among specimen racks which are in the standby state in the buffer sections inside the buffer unit to be the carrying destination target, a specimen rack in which it is assumed that the processing is not executed for a while because of a waiting state for reexamination or others is temporarily carried into another buffer unit whose buffer section has the vacancy so as to make the vacancy in the buffer section inside the buffer unit, so that the carrying of the specimen rack which needs to be analyzed is possible.

When the buffer section can be secured in the corresponding buffer unit or when it is required to execute the reexamination, the specimen rack, which has been temporarily moved to another buffer unit, can be carried and returned again to the buffer unit which has been in the standby state prior to the temporal evacuation. Moreover, if the functional module or the additional module which requires the corresponding specimen rack is not adjacent to the buffer unit prior to the evacuation, the corresponding specimen rack can be directly carried from the buffer unit in which it is evacuating to the buffer unit adjacent to the functional module or the additional module which requires the corresponding specimen rack. In this manner, a period of time during when the supplying is impossible due to the number of storage specimen racks inside the buffer unit can be shortened, so that this shortening contributes to improvement of the processing performance in the entire system.

Obviously, if the specimen rack which has been carried out can be directly carried into the module carrying-in/out standby section 310, the specimen rack is carried to the buffer section 302, the functional module 400, or others (steps 1203, 1208, and 1214) in accordance with the carrying destination designated by the operating-section computer 1 (steps 1202, 1204, 1205, and 1209).

If the carrying destination of the specimen rack which has been notified from the operating-section computer 1 is another buffer unit 300 or if the collection carrying operation is instructed, the fact that the specimen rack to be carried out from this unit to the rack carrying unit 200 has been detected is notified together with the ID information capable of specifying the specimen rack (step 1210).

Moreover, a process is prepared for the buffer unit 300, the process outputting an abnormal alarm for the designation of the carrying destination (step 1215) if an unspecific carrying destination is designated as the designated carrying destination notified from the operating-section computer 1 so that the operating-section computer 1 is urged to collect the corresponding specimen rack.

Next, with reference to FIG. 12, the carrying-out process of the specimen rack from the buffer unit 300 to the rack carrying unit 200 will be described.

The specimen rack held inside the buffer unit 300 receives a rack carrying-out request (step 1301) from the operating-section computer 1, so that the carrying-out operation is started.

There is a case that, as the carrying destination of the specimen rack to be carried out from the buffer unit 300, the carrying to another buffer unit 300 or the instruction of the collection carrying operation is designated.

In the present system, a specimen rack in which a precision control specimen to be carried to the cold storing section 303 of the buffer unit 300 is provided is assigned to a slot position inside the cold storing section 303 whose usage is not permitted in the carrying-in operation from the rack carrying unit 200, and the specimen rack is maintained at the slot position of the cold storing section 303 to which it is assigned once until it is collected from the main system. If it is carried out so as to be analyzed in another buffer unit 300 (step 1303), the permission of use inside the cold storing section 303 is not released. If it is carried out so as to be collected (step 1303), the permission of use inside the cold storing section 303 is released (step 1304). In this manner, when the specimen rack which needs to be in the standby state in the cold storing section is required in the analyzing unit adjacent to each of the plurality of buffer units existing inside the system, the specimen rack can be handled without securing a standby place for each of the buffer units. In this manner, the number of precision control specimens to be loaded into the system can be reduced. Moreover, since the precision control specimen is in the standby state inside the system, the quality control can be simply confirmed, and a usage validity date of the precision control specimen can be easily judged.

In the present system, the specimen rack to be carried to a buffer section 302 of the buffer unit 300 is assigned to a slot position inside the buffer section 302 whose usage is not permitted in the carrying-in operation from the rack carrying unit 200, and the specimen rack is maintained at the slot position of the buffer section 302 to which it is assigned once until it is carried out to the rack carrying unit 200, and therefore, the permission of use inside the buffer section 302 is released in both cases of the carrying-out process for the analysis in another buffer unit 300 and the carrying-out process for the collection (step 1305).

Once the permissions of use of the cold storing section 303 or the buffer section 302, which is managed by the buffer unit 300, is released, the sections can be used for a next specimen rack to be carried therein.

When the specimen rack to be carried out from this unit is detected, the buffer unit 300 notifies the rack carrying unit 200 of the detection of the rack to be carried out together with the ID information capable of specifying the specimen rack (step 1306).

When the rack carrying unit 200 can handle the carrying-out operation in response to the notification of the detection of the specimen rack to be carried out notified from the buffer unit 300, it notifies the buffer unit 300 of the carrying-out preparation request together with the information of the belt mechanism 210 by which the corresponding rack is to be carried out.

Based on the carrying-out preparation request from the rack carrying unit 200, the buffer unit 300 uses the specimen-rack transferring mechanism 330 of the buffer unit 300 to move the corresponding rack onto the belt mechanism 210 to be used for the carrying-out operation, so that the specimen rack is carried out therefrom (step 1308).

In the carrying process of the specimen rack in the buffer unit 300, there is a rule that a priority (ex. emergent rack>general rack>washing rack) is put on each specimen rack carried into the buffer unit 300 so that a rack having a higher priority should be preferentially carried. Therefore, a carrying control logic is adopted, the carrying control logic starting the rack carrying process based on the type or the designated priority order of the specimen rack to be carried.

Moreover, there is a rule that a group of racks whose operations have been started (a rack forming the same group with the rack which has been carried to the functional module 400 or the additional module 450) cannot be passed. Therefore, a carrying control logic starting the rack carrying process in consideration of management of the group is adopted.

In the carrying process of the specimen rack in the buffer unit 300, carrying operation requests for carrying the specimen rack which has been carried in the buffer unit 300 and for carrying the specimen rack which has been carried out from the functional module 400 are overlapped with each other sometimes.

Moreover, when a specimen rack to be the carrying target is always detected at the same carrying position, a case that it is difficult to start the carrying process of the specimen rack occurs.

In order to avoid the carrying problem described above, a carrying control logic is adopted in the buffer unit 300, the carrying control logic putting a priority order on the selection of the carrying start position so as to lower the priority order of the carrying process start from the carrying position at which the carrying process of the specimen rack has been already started.

In the buffer unit 300, the specimen-rack carrying-in/out operation to/from the carrying unit 200, the specimen-rack carrying-in/out operation to/from the functional module 400, and the specimen-rack carrying-in/out operation to/from the additional module 450 are required, and a plurality of carrying operation requests can be received simultaneously.

In the actual specimen-rack carrying operation described above on a plurality of carrying passages, detection orders of the specimen-rack carrying requests which randomly occur are dynamically changed. That is, a control logic is adopted, the control logic ranking the detection order of the carrying request for the passage on which the carrying operation has been actually executed as a detection target of a bottom of the rank, and preferentially performing the detection of the carrying request for the specimen rack for which the operation has not been started yet.

The cold storing section 303 of the buffer unit 300 holds a precision control specimen and has a cold storing mechanism so as to prevent evaporation of the specimen, and therefore, its contact with outer air affects the precision control specimen provided in the specimen rack held in the cold storing section 303. In order to avoid this problem, a mechanism control logic is adopted, the mechanism control logic opening and closing a door to only an extent required for access to the specimen rack in the carrying of the specimen rack into the cold storing section 303 or the carrying of the specimen rack out from the cold storing section 303.

As a support for when the rack carrying unit 200 is broken, a backup operation function is prepared for the buffer unit 300. This is a function which directly loads a specimen rack into the buffer unit 300 from a rack loading section 320 from which the rack can be directly loaded and which reads the ID information of the loaded specimen rack and the ID information of the rack and the specimen to be provided from the ID identifying unit 321 used for identifying the ID of the specimen to be provided in the specimen rack so that the corresponding rack can be analyzed.

A judgment logic to be used when the specimen rack inside the buffer unit is carried out to the specimen-rack carrying section will be described. In the buffer unit having the specimen rack to be carried out, it is judged whether or not the specimen-rack carrying section has already started the specimen-rack carrying operation to/from another buffer unit, and, if the judgment is made as the operable state, the carrying-out operation of the specimen rack from the corresponding buffer unit starts.

Moreover, in the buffer unit, it is also judged whether or not another specimen-rack carrying operation (such as the carrying-in/out operation with the functional module) has already been started, and, if the judgment is made as the operable state, the carrying-out operation of the specimen rack in the carrying unit starts.

Next, with reference to FIG. 9, the specimen-rack carrying-in process from the rack carrying unit 200 to the buffer unit 300 will be described.

The buffer unit 300 can be informed of the belt mechanism 210 to be used for carrying the specimen rack and the ID information capable of specifying the rack to be carried in which has been notified as the rack carrying-in preparation request from the rack carrying unit 200. The specimen-rack transferring mechanism 330 is moved to a position of the belt mechanism 210 to be the carrying-in target, and receive the specimen rack to be carried from the rack carrying unit 200.

When the reception of the specimen rack is completed, the operating-section computer 1 is notified of the ID information capable of specifying the rack to be carried in so as to be informed of the arrival of the specimen rack (step 1001).

Based on the ID information notified from the buffer unit 300, the operating-section computer 1 notifies this unit of the carrying destination of the specimen rack which has been carried in the buffer unit 300.

In the buffer unit 300, prior to the carrying of the arrived specimen rack based on the carrying destination of the specimen rack designated by the operating-section computer 1, the designated carrying destination is identified in the buffer unit 300 (steps 1002, 1005, 1007, 1008) so as to acquire the permission of use for the vacant slot position existing in the cold storing section 303 or the buffer section 302 inside this unit (steps 1003 and 1004).

A purpose of the acquisition of the permission of use for the vacant slot position is for a state that, for example, when the designated carrying destination of the specimen rack which has been carried therein is the functional module 400, if a carrying-in possible number of specimen racks in this functional module has already been carried inside the functional module of the carrying destination, a carrying impossible case occurs. Due to this state, if the specimen rack which has been carried in the buffer unit 300 remains in the rack carrying-in/out standby section 301, another specimen rack cannot be carried out from the buffer unit 300 to the rack carrying unit 200, and therefore, the purpose is for avoiding this problem.

A carrying control logic is adapted in the buffer unit 300, the carrying control logic carrying the specimen rack such that, in order to avoid the above-described state that the specimen rack remains in the rack carrying-in/out standby section 301, if it is judged that the specimen rack cannot be loaded into the functional module 400 or the additional module 450 to be the designated carrying destination, the specimen rack is carried once for evacuation (step 1010) to the cold storing section 303 or the buffer section 302 which have acquired the permission of use so as to release the rack carrying-in/out standby section 301, and the evacuated specimen rack is carried after the state of the functional module 400 or the additional module 450 transits to the load possible state.

Obviously, if the specimen rack which has been carried in the rack carrying-in/out standby unit 301 can be directly carried, the specimen rack is carried to the buffer section 302, the functional module 400, or the additional module 450 in accordance with the carrying destination designated by the operating-section computer 1 (steps 1006 and 1009).

A judgment logic to be used when the specimen rack which has been carried by the specimen-rack carrying section is carried into the buffer unit will be described. In the specimen-rack carrying section, it is judged whether or not the buffer unit in which the specimen rack is to be carried has already started another specimen-rack carrying (carrying-in/out) operation to/from the adjacent functional module or the specimen-rack carrying unit, and, if the judgment is made as the operable state, the carrying-in operation of the specimen rack to the corresponding buffer unit starts.

Moreover, in the specimen-rack carrying unit, it is judged whether or not there is a vacancy of the buffer section which can hold a new specimen rack inside the buffer unit in which the specimen rack is to be carried, and, if the judgment is made as the operable state, the carrying-in operation of the specimen rack in the corresponding buffer unit starts.

If there is no vacancy of the buffer section which can hold the new specimen rack inside the buffer unit in which the specimen rack is to be carried by the specimen-rack carrying section, the operating-section computer searches other buffer unit inside the system, which has a vacancy of a buffer which can temporarily hold another specimen rack inside the buffer unit in which the specimen rack is to be carried. If other buffer unit which can hold the evacuated specimen rack is found, the evacuation operation of the specimen rack is instructed to the buffer unit which stores the specimen-rack carrying unit/the evacuated specimen rack and the buffer unit to be an evacuation destination.

Moreover, for the buffer unit 300, if an unspecific carrying destination is designated as the designated carrying destination notified from the operating-section computer 1, a process of outputting an abnormal alarm for the carrying destination designation (step 1011) so that the operating-section computer 1 is urged to collect the corresponding specimen rack is also prepared.

All the operation results of these carrying operations are stored in an external storage device of the operating-section computer 1, and a log information output function for displaying the operation results is provided. Therefore, an operator can trace when and to which place a specific specimen is moved.

Moreover, the specimen provided in the specimen rack to be loaded into the system is analyzed by a plurality of functional modules or additional modules which configure the corresponding system in some cases. In such a case, if the carrying is performed without consideration of a load due to a processing period of time in all the functional modules or additional modules in which the specimen is carried, there is a risk that the processing performance of the entire system is affected.

Moreover, the start of the carrying always from a functional module or additional module which is the closest to a loading position of the specimen rack into the system occurs a buffer unit having high load in the carrying operations because of a large number of the held specimen racks and a buffer unit having little load in the carrying operations because the specimen rack is difficult to arrive, and therefore, the processing performance of the entire system is adversely affected.

In such a case, when the specimen rack is loaded, a carrying destination module of the specimen rack to be loaded into the system is selected based on a load rate determined by the number of processing requests to be assigned to the functional modules or additional modules, the processing time in the functional module, or others.

By providing such a carrying process, vacant time in analysis in the functional module or others inside the system can be shortened, so that the shortening contributes to the improvement of the processing performance of the entire system. Moreover, by determining a next carrying destination in the completion of the process in the functional module or others, even if a functional module or an additional module in which the analysis is planned at the time of loading the specimen rack cannot be used for some reason, a rack carrying process so as to avoid these modules can be achieved.

Further, these flows may be systematically judged by the operating-section computer or individually judged in accordance with the state of each unit.

SYMBOL EXPLANATION 1 operating-section computer
2 operating-section CRT (information displaying section)
3 network connection
100 sampler unit
101 loading section
102 storing section
103 load-rack moving unit
104 rack ID identifying unit
105 specimen-container-height detecting unit
106 specimen ID identifying unit
107 specimen-container rotating unit
108 storage-rack moving unit
109 emergent-specimen loading section
121 loading tray
122 loading buffer section
123 loading lever
131 storing tray
132 storing buffer section 133 storing lever
200 rack carrying unit
201 feeding lane
202 returning lane
210 belt mechanism
300a and 300b buffer unit
301 rack carrying-in/out standby section
302 buffer section
303 cold storing section
310 module carrying-in/out standby section
311 rack carrying section
320 one-rack loading out section (one-rack loading section)
321 ID identifying unit
330 rack transferring mechanism
350 module carrying-in/out standby position
360 rack moving mechanism
400a and 400b functional module
450 additional module
500 specimen rack
501 specimen rack ID
502 specimen container
503 specimen ID
601 step of judgment on rack-load possibility/impossibility
602 step of judgment on detection of carrying-in rack of emergent-specimen loading section
603 step of judgment on detection of carrying-in rack of specimen loading section
604 step of read of load rack ID
605 step of determination of load-rack carrying destination
606 step of judgment on designation of load-rack carrying destination
607 step of notification of buffer-unit carrying-in preparation request
608 step of execution of load-rack collecting operation
609, 705, and 909 step of judgment on completion of buffer-unit carrying-in preparation
610, 706, and 910 step of execution of rack carrying-in operation into buffer unit
701 step of judgment on detection of buffer-unit carrying-out rack
702 step of judgment on carrying-in permission of carrying-destination buffer unit
703 step of notification of buffer-unit carrying-in/out preparation request
704 step of judgment on completion of buffer-unit carrying-out preparation
801 step of judgment on detection of buffer-unit-collection carrying-out rack
802 and 902 step of notification of buffer-unit carrying-out preparation request
803 and 903 step of judgment on completion of buffer-unit carrying-out preparation
804 step of execution of collection-rack carrying operation
805 step of judgment on state of rack storing section
806 step of alarm output for detection of full state of rack storing section
807 step of execution of rack-collection operation into storing section
901 step of judgment on detection of buffer-unit round-carrying-out rack
904 step of execution of round-rack carrying operation
905 judgment on rack-load possibility/impossibility
906 step of read of load rack ID
907 step of determination of load-rack carrying destination
1001 step of arrival of rack into buffer unit
1002 and 1202 step of judgment on rack carrying into storing section
1003 step of acquisition of permission of use of storing section
1004 step of acquisition of permission of use of buffer section
1005 and 1204 step of judgment on buffer standby
1006 step of execution of carrying operation into buffer section
1007 step of judgment on functional module/additional module carrying
1008 and 1206 step of judgment on functional module/additional module carrying-in permission
1009 and 1208 step of execution of functional module/additional module carrying operation
1010, 1207, and 1212 step of execution of evacuation carrying operation into buffer section
1011 step of alarm output for unspecific carrying destination
1101 step of judgment on functional module/additional module carrying-in
1102 step of notification of functional module/additional module carrying-out preparation request
1103 step of judgment on completion of functional module/additional module carrying-out preparation
1104 step of functional module/additional module carrying-in operation
1201 step of reception of rack carried out from functional module/additional module
1203 step of execution of rack carrying operation to standby position
1205 step of judgment on rack carrying destination to functional module/additional module
1209 step of judgment on rack carrying destination to another buffer unit
1210 step of report of detection of rack carried out to rack carrying unit
1211 and 1307 step of judgment on carrying-out preparation request from rack carrying unit
1213 and 1305 step of release of permission of use of buffer section
1214 step of execution of rack carrying-out operation from buffer unit
1215 step of alarm output for unspecific carrying destination
1301 step of judgment on rack carrying-out request
1302 step of judgment on carrying-out-rack standby section
1303 step of judgment on carrying-out-rack carrying destination
1304 step of release of permission of use of cold storing section
1306 step of report of detection of rack carried out to rack carrying unit
1308 step of execution of rack carrying-out operation from buffer unit

The invention claimed is:

1. A method of carrying a specimen in an automatic analyzer, including providing the automatic analyzer with:
a plurality of functional modules each of which is configured to execute a process including analysis of the specimen,
a plurality of buffer units paired with the functional modules, each of the buffer units including plural buffer sections which are arranged upstream of a respectively paired one of the functional modules where the specimen waits in a standby state, and a rack carrying section which carries the specimen between the buffer unit and the respectively paired functional module,
a sampler unit having a loading unit to load the specimen and a storage unit to store the specimen,
a rack carrying unit including a first belt lane mechanism which carries the specimen from the loading unit to one of the functional modules and a second belt lane mechanism which carries the specimen from one of the functional modules to the storage unit, and
a rack transferring mechanism included in each of the buffer units which can transfer the specimen bi-directionally from the rack carrying unit to either of the buffer sections or the rack carrying section,
wherein the method comprises:
loading the specimen into the loading unit;
determining one of the functional modules as a carrying destination and a carrying timing of the specimen based on operational states of the buffer units, and functional modules;
carrying the specimen from the loading unit towards the carrying destination with the first belt lane mechanism;
determining that the specimen is to be collected in the storage unit;
directly transferring the specimen, which has reached the rack transferring mechanism by the first belt lane mechanism, with the rack transferring mechanism onto the second belt lane mechanism; and
carrying the specimen to the storage unit with the second belt lane mechanism.

2. The method of carrying the specimen in the automatic analyzer of claim 1, wherein
when the specimen is to be collected, the rack transferring mechanism directly transfers the specimen onto the second belt lane mechanism such that the specimen does not move through the buffer sections.

3. The method of carrying the specimen in the automatic analyzer of claim 1, wherein the specimen is loaded into the loading unit in a specimen rack.

4. An automatic analyzing system comprising:
a plurality of functional modules each of which is configured to execute a process including analysis of a specimen;
a plurality of buffer units paired with the functional modules, each of the buffer units including plural buffer sections which are arranged upstream of a respectively paired one of the functional modules where the specimen waits in a standby state, and a rack carrying section which carries the specimen between the buffer unit and the respectively paired functional module;
a sampler unit having a loading unit for loading the specimen and a storage unit for storing the specimen;
a rack carrying unit including a first belt lane mechanism which carries the specimen from the loading unit to one of the functional modules and a second belt lane mechanism which carries the specimen from one of the functional modules to the storage unit;
a rack transferring mechanism included in each of the buffer units which transfers the specimen bi-directionally from the rack carrying unit to either of the buffer sections or the rack carrying section; and
a controller configured to control the rack carrying unit according to a carrying destination and a carrying timing of the specimen loaded to the loading unit based on operation states of the buffer units and the functional modules and the requested analysis items of the specimen,
wherein, the controller is configured to control the rack transferring mechanism so that the specimen, which has reached the rack transferring mechanism through the first belt lane mechanism, is directly transferred onto the second belt lane mechanism and carried to the storage unit.

5. The automatic analyzing system of claim 4, wherein
the controller is configured to control the rack transferring mechanism so that the specimen is directly transferred onto the second belt lane mechanism and does not move through the buffer sections.

6. The automatic analyzing system of claim 4, wherein the specimen is loaded into the loading unit in a specimen rack.

7. The automatic analyzing system according to claim 4,
wherein the buffer unit is connectable to another functional module different from the functional module paired therewith, and
the controller is configured to control the rack carrying unit in accordance with a condition judged by the controller that indicates whether a carrying-in/out operation of each of the functional modules connected therewith is allowed.

8. The automatic analyzing system according to claim 4,
wherein, based on states of the functional modules arranged so as to be paired with the buffer units, the controller is configured to control each of the rack carrying sections to carry a specimen rack, which is holding a specimen, to a paired functional module.

9. The automatic analyzing system according to claim 4,
wherein, when a specimen rack, which is holding a specimen, for which a process is completed is carried out from the buffer unit to the rack carrying unit, the controller controls the rack carrying unit in accordance with a state of the rack carrying unit.

10. The automatic analyzing system according to claim 4,
wherein a precision control specimen rack carried into the buffer unit is stored in a cold storing standby position inside the buffer unit, and
wherein the precision control specimen rack is carried to a buffer section or any functional module based on a judgment made by the controller which judges whether it is necessary for a functional module to use a precision control specimen held in the precision control specimen rack.

11. The automatic analyzing system according to claim 6, further comprising:
a rack ID identification unit configured to read an ID of the specimen rack when inside the rack carrying unit,
wherein, based on an instruction from the controller, the controller is configured to control the rack carrying unit in accordance with a condition judged by the controller that indicates whether a carrying-in/out operation to/from each of the buffer units is allowed.

12. The automatic analyzing system according to claim 11,
wherein, based on a carrying instruction from the controller, the controller controls the rack carrying unit and rack transferring mechanism to carry the specimen rack to one of the buffer units.

13. The automatic analyzing system according to claim 11,
wherein, based on a state of each of the plurality of buffer units, the controller is configured to control the rack carrying unit to carry a specimen rack so as to be carried to a buffer unit which can hold the specimen rack in the standby state.

14. The automatic analyzing system according to claim 11,
wherein, based on a state of each of the plurality of buffer units, the controller is configured to control the rack carrying unit so as to be collected from the one of the buffer units which holds the specimen rack in the standby state.

15. The automatic analyzing system according to claim 11, wherein, based on a carrying-in possible state and a carrying-out possible state of each of the plurality of buffer units, the controller is configured to control the rack transferring mechanism and the rack carrying unit to carry a specimen rack stored in one of the buffer units to be carried to another of the buffer units.

16. The automatic analyzing system according to claim 15, wherein the carrying-in possible state is judged based on at least one of the rack carrying unit not having started a carrying operation of another specimen rack yet, a vacant position available inside one of the buffer units in which a new specimen rack is to be carried and can be held, and if the vacant position is unavailable inside the one of the buffer units in which a new specimen rack is to be carried another of the buffer units has a vacant position available in which the new specimen rack can be held.

17. The automatic analyzing system according to claim 16, wherein each of the buffer units are respectively connectable to another functional module in a direction opposite to that of the functional module with which each of the buffer units is respectively paired, and the carrying process of the specimen rack is controllable as judging a condition which allows the carrying-in/out operation of each of the functional modules connected therewith.

18. The automatic analyzing system according to claim 16, wherein the first and second belt lane mechanisms arranged in parallel with each other, and the rack transferring mechanism included in each of the buffer units can transfer the specimen rack bi-directionally to/from the buffer sections and the rack carrying section.

19. The automatic analyzing system according to claim 8, wherein, if a specimen rack cannot be loaded into a paired functional module the specimen rack is stored in a rack standby position inside the buffer unit.

20. The automatic analyzing system according to claim 9, wherein, if a specimen rack for which the process is completed cannot be loaded onto the rack carrying unit, the specimen rack for which the process is completed is stored in a rack standby position inside the buffer unit.

21. The automatic analyzing system according to claim 10, wherein, for the precision control specimen rack, the cold storing standby position of the buffer unit which has been assigned thereto once can be used during from when the precision control specimen rack is loaded into the automatic analyzing system until the precision control specimen rack is collected therefrom.

22. The method of carrying the specimen in the automatic analyzer according to claim 1, wherein the first belt lane mechanism is configured to carry the specimen from the loading unit to any one of the functional modules and the second belt lane mechanism is configured to carry the specimen from any one of the functional modules to the storage unit.

\* \* \* \* \*